(12) United States Patent
Svanborg et al.

(10) Patent No.: US 7,053,185 B1
(45) Date of Patent: May 30, 2006

(54) LACTALBUMIN PRODUCTION PROCESS

(75) Inventors: Catharina Svanborg, Lund (SE); Per Anders Hakansson, Lund (SE); Malin Wilhelmina Svensson, Lund (SE)

(73) Assignee: HAMLET Pharma AB, Lund (SE)

( * ) Notice: Subject to any disclaimer, the term of this patent is extended or adjusted under 35 U.S.C. 154(b) by 0 days.

(21) Appl. No.: 09/554,704

(22) PCT Filed: Nov. 23, 1998

(86) PCT No.: PCT/IB98/01919

§ 371 (c)(1),
(2), (4) Date: Aug. 15, 2000

(87) PCT Pub. No.: WO99/26979

PCT Pub. Date: Jun. 3, 1999

(30) Foreign Application Priority Data

Nov. 21, 1997 (GB) .................................. 9724725.8
Jun. 5, 1998 (GB) .................................. 9812202.1

(51) Int. Cl.
*C07K 1/00* (2006.01)

(52) U.S. Cl. ...................... 530/366; 530/350; 530/300; 530/394; 530/365; 530/414; 530/416; 426/580; 426/583; 435/7.1

(58) Field of Classification Search ................ 530/350, 530/366, 394, 414, 416, 300, 365; 426/580, 426/583; 435/7.1

See application file for complete search history.

(56) References Cited

FOREIGN PATENT DOCUMENTS

FR      2 671 697     7/1992
WO     WO 96 04929   2/1996

OTHER PUBLICATIONS

M. Jegouic et al, "Baric oligomerization in α-lactalbumin/β-lactoglobulin mixtures", Jour. of Agricultural and Food Chem., 45(1):19-22 (1997).
A. Hakanson et al., Proc. Natl, Acad. Sci. USA, (1995) 92, 8064-8068.
Kronman et al., 1965 Biochem, 4 518-525.
Dolgikh et al., Febs Lett, (1981) 136, 311-315.
Dolgikh et al., Febs Lett, (1984) 165:88-92.
Ohgushi & Wada, 1983, A Febs Lett 164:21-25.
Pfeil et al., 1987 Biochem Biophys Acta, 911:114-116.
Kuwajima 1996 Faseb J., 1:102-109.
Shulman et al., 1995 J. Mol. Bol. 253, 651-657.
J. Bitman et al., J. Ped. Gast. Nutr. 1983:521-524.
Hall, L., Emery, D.C., Davies, M.S., Parker, D., and Craig, R.K., "Organization and Sequence of the Human Alpha-lactalbumin Gene", Biochem J. 242:725-742, 1987.
Davies, M.S., West, L.F., Davis M.B., Povey, S. and Craig R.K., "The Gene for human alpha-lactalbumin is Assigned to Chromosome 12q13", Ann Hum Genet, 1987.
Peng et al., "A Protein Dissection Study of a Molten Globule", Biochemistry 33:2136-41, 1994.
Zeisel et al., J. Nutr. 1986, 116, 50-58.

*Primary Examiner*—Jon Weber
*Assistant Examiner*—Hope A. Robinson
(74) *Attorney, Agent, or Firm*—Burns, Doane, Swecker & Mathis, L.L.P.

(57) ABSTRACT

A method for producing an oligomeric form of α-lactalbumin which is in the molten globule-like state is described. The method suitably comprises exposing a source of α-lactalbumin in which the α-lactalbumin is preferably in the molten globule-like state, to an ion exchange medium which has been pre-treated with casein or an active component thereof, such as oleic acid, and recovering α-lactalbumin in an oligomeric form therefrom. Pre-treatment of the ion exchange medium, particularly with casein derived from human milk, has been found to significantly improve yields of the oligomeric form of α-lactalbumin and means that it can be readily isolated from readily available sources such as bovine α-lactalbumin. This form of α-lactalbumin is useful therapeutically, in particular as an antibacterial agent and also as an anti-cancer therapeutic.

49 Claims, 12 Drawing Sheets

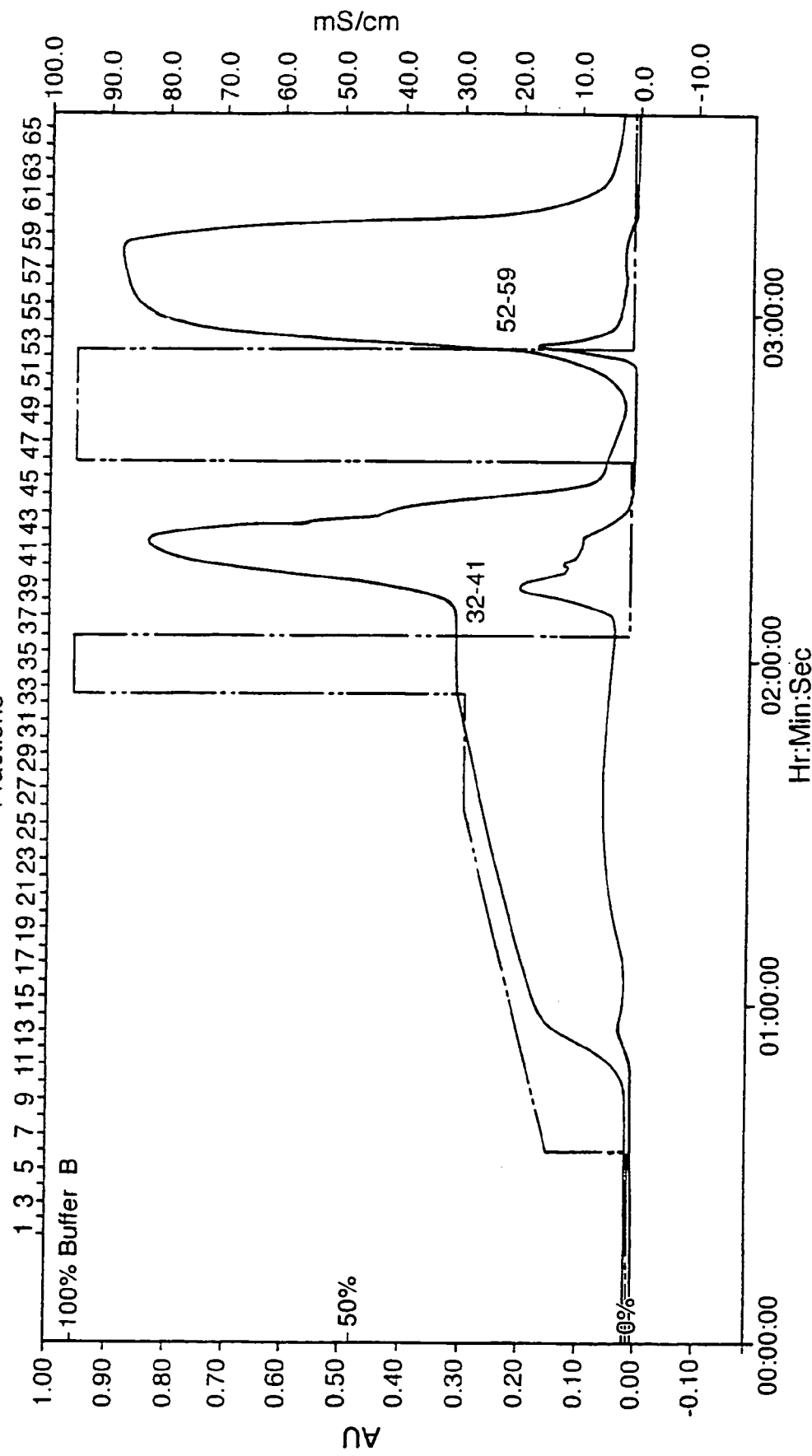

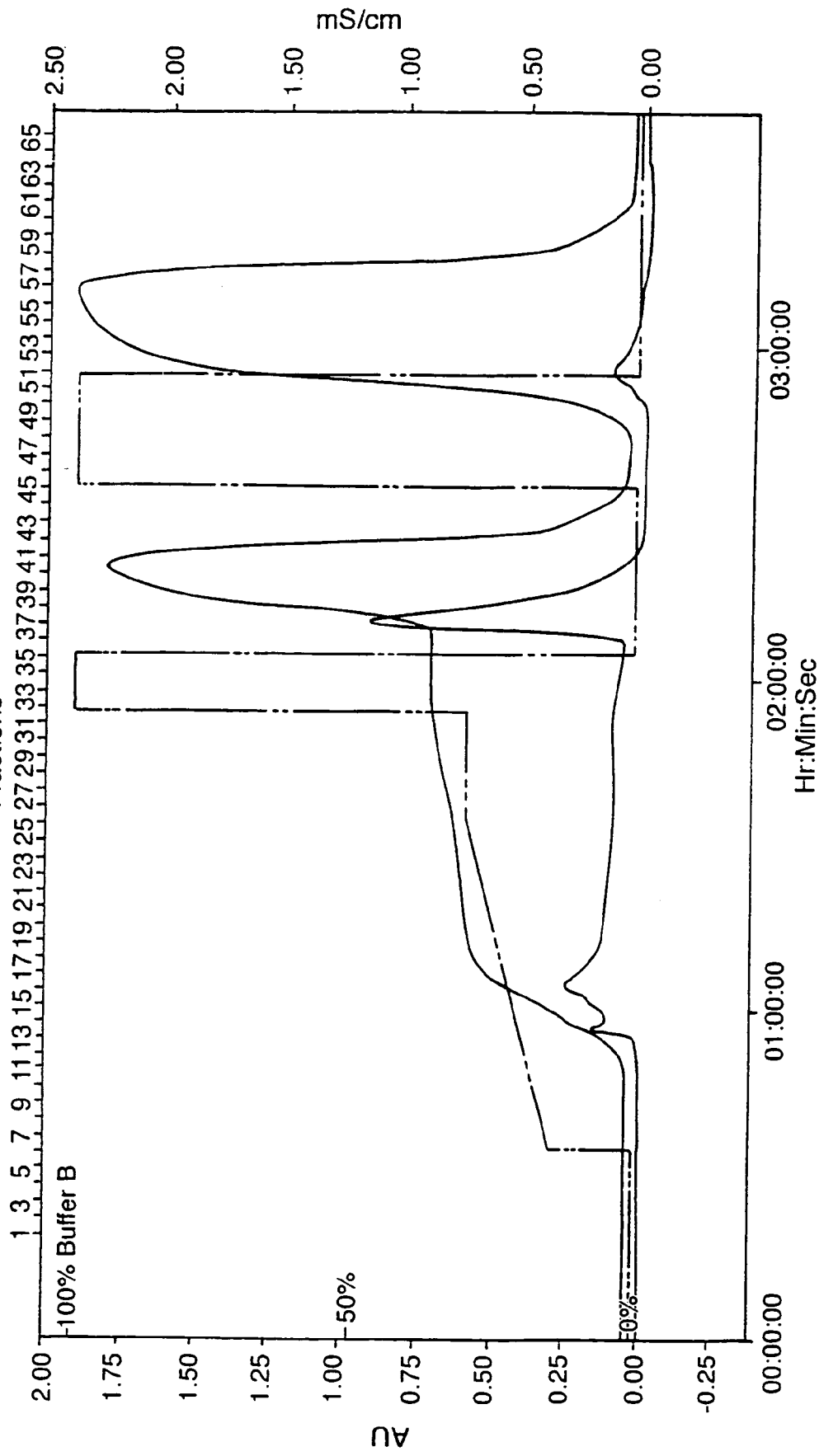

SEQUENCE LISTING

```
<160> NUMBER OF SEQ ID NOS: 8

<210> SEQ ID NO 1
<211> LENGTH: 30
<212> TYPE: PRT
<213> ORGANISM: Artificial Sequence
<220> FEATURE:
<223> OTHER INFORMATION: amino acid sequence of alpha-lactalbumin (HLA)

<400> SEQUENCE: 1

Lys Gln Phe Thr Lys Cys Glu Leu Ser Gln Leu Leu Lys Asp Ile Asp
 1               5                  10                  15

Gly Tyr Gly Gly Ile Ala Leu Pro Pro Leu Ile Asp Thr Met
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: amino acid sequence of the protein bands of MAL
<220> FEATURE:
<221> NAME/KEY: VARIANT
<222> LOCATION: 6
<223> OTHER INFORMATION: Xaa = Any Amino Acid

<400> SEQUENCE: 2

Lys Gln Phe Thr Lys Xaa Glu Leu Ser Gln Leu Leu Lys Asp Ile Asp
 1               5                  10                  15

Gly Tyr Gly Gly Ile Ala Leu Pro Pro Leu Ile Asp Thr Met
            20                  25                  30
```

-continued

```
<210> SEQ ID NO 3
<211> LENGTH: 10
<212> TYPE: PRT
<213> ORGANISM: Artificial Sequence
<220> FEATURE:
<223> OTHER INFORMATION: amino acid sequence of the protein bands of MAL
<220> FEATURE:
<221> NAME/KEY: VARIANT
<222> LOCATION: 6
<223> OTHER INFORMATION: Xaa = Any Amino Acid

<400> SEQUENCE: 3

Lys Gln Phe Thr Lys Xaa Glu Leu Ser Gln
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: amino acid sequence of the protein bands of MAL

<400> SEQUENCE: 4

Lys Gln Phe Leu Lys Arg Pro Lys Thr Pro
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: amino acid sequence of the protein bands of MAL
<220> FEATURE:
<221> NAME/KEY: VARIANT
<222> LOCATION: 5, 6, 9
<223> OTHER INFORMATION: Xaa = Any Amino Acid

<400> SEQUENCE: 5

Lys Gln Phe Thr Xaa Xaa Glu Leu Xaa Gln
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: amino acid sequence of the protein bands of MAL
<220> FEATURE:
<221> NAME/KEY: VARIANT
<222> LOCATION: 5, 6, 9
<223> OTHER INFORMATION: Xaa = Any Amino Acid

<400> SEQUENCE: 6

Lys Gln Asn Ile Xaa Xaa Glu Ser Xaa Val
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: amino acid sequence of the protein bands of MAL
<220> FEATURE:
<221> NAME/KEY: VARIANT
<222> LOCATION: 5, 6, 9
<223> OTHER INFORMATION: Xaa = Any Amino Acid

<400> SEQUENCE: 7
```

-continued

```
Lys Gln Phe Thr Xaa Xaa Glu Tyr Xaa Asn
1               5                   10

<210> SEQ ID NO 8
<211> LENGTH: 6
<212> TYPE: PRT
<213> ORGANISM: Artificial Sequence
<220> FEATURE:
<223> OTHER INFORMATION: amino acid sequence of the protein bands of MAL
<220> FEATURE:
<221> NAME/KEY: VARIANT
<222> LOCATION: 6
<223> OTHER INFORMATION: Xaa = Any Amino Acid

<400> SEQUENCE: 8

Lys Gln Phe Thr Lys Xaa
1               5
```

LACTALBUMIN PRODUCTION PROCESS

This application is a national stage application under 35 U.S.C. § 371 of PCT/IB98/01919, filed on Nov. 23, 1998, which claims priority to GB 9724725.8, filed on Nov. 21, 1997, and GB 9812202.1, filed on Jun. 5, 1998.

The present invention relates to a process for the preparation of a therapeutic protein complex, and to apparatus and reagents for use in the process.

Monomeric α-lactalbumin is the most abundant protein in human milk whey. This 14 KDa protein has been extensively characterised and the crystal structure has been resolved. There are four α-helices and one triple stranded β-sheet, which is found at the C-terminal end of the protein. A high affinity Ca2+ binding site is coordinated by the side chain carboxylates of Asp82, Asp87, Asp88 and the carbonyl oxygen of Lys79 and Asp84, with two water molecules.

The native monomer is a component of the lactose synthase complex, and alters the substrate specificity of the galactosyl transferase from N-acetylglucosamine to glucose, with subsequent synthesis of lactose.

A fraction from human milk containing an oligomeric complex, described as multimeric α-lactalbumin or MAL, has previously been reported which has different biological properties to the monomeric form. In particular, the oligomeric complex is reported as having therapeutic applications both in the field of antibiotic (WO96/04929) and cancer therapy (A. Håkansson et al., Proc. Natl. Acad. Sci USA, (1995) 92, 8064–8068). In particular, the oligomeric form of α-lactalbumin induces apoptotic cell death in cancer cells and immature cells, but not in healthy cells. These observations suggested that the protein acquires novel biological properties after conformational switching.

It is known that α-lactalbumin undergo conformational switching when exposed to low pH. The A state or molten globule state has native secondary structure, but less well defined tertiary structure than the native state. Similar states of α-lactalbumin can form also at neutral pH, upon removal of the tightly bound $Ca^{2+}$ ion, reduction of disulphide bonds or at elevated temperatures.

MAL was obtained by passing a casein fraction of milk, particularly human milk, down an ion exchange column, specifically a Diethylaminoethyl ("DEAE")-[tri-hydroxymethyl-aminomethane] ("TRIS")-Acryl M column using an NaCl gradient. A pool containing MAL which was active therapeutically was obtained. In addition, the conversion of commercially available monomeric α-lactalbumin to the active form was reported.

The applicants have found that the active form of α-lactalbumin precipitated with casein rather than with the whey fraction, at low pH, and eluted with high salt during ion-exchange chromatography. Spectroscopic characterisation of the active form suggested that it consisted, at least in part, of folding intermediates of α-lactalbumin in stable aggregates.

The conformation and biological activities of proteins is thought to be under thermodynamic control, and dictated by the amino acid sequence. Recently, it has become evident that some proteins can be trapped in folding states with higher free energy, and that such folding variants of a single protein can acquire different biological functions. The conformational switch of the prion protein for example leads to the formation of a disease forming isoform, with the same amino acid sequence, and no post-translational modifications to distinguish the two. The prion protein first changes to the molten globule state and then proceeds to a non-reversible β-sheet rich form.

It appears that α-lactalbumin is a further case of a protein that acquires novel functions after conformational switching. As in the prion system, the two molecular forms of the protein have identical amino acid sequence, with no post-translational modifications as detected by mass spectrometry. Without being bound by any theoretical considerations, it is proposed that the relative folding instability of α-lactalbumin allows the protein to undergo structural transitions and attain new essential functions.

Protein folding variants like prions, amyloid and lysozyme are associated with disease, and are thought to directly trigger tissue destruction. The α-lactalbumin variant in contrast, may have beneficial effects. It may indeed represent a physiologic function for folding variants, that has gone astray in the case of prions and amyloid fibrils.

The altered folding state of α-lactalbumin however drastically alters its interactions with tumour cells. Healthy cells have limited longevity. When they are old, cell death programs are activated, and the cells die by apoptosis. Tumour cells often inactivate the cell death programs, multiply and survive. Many approaches have been taken to limit tumour cell survival, to make cells revert to a differentiated phenotype or to make them undergo apoptosis. In its altered folding state, α-lactalbumin forms MAL which appears to target immature cells and tumour cells and activate programmed cell death. There is clearly applications for this in cancer therapy.

With a greater understanding of the structure of MAL, the applicants have found an improved way of producing biologically active MAL in greater yields and from a greater variety of α-lactalbumin sources.

Thus the present invention provides a method of producing a biologically active form of α-lactalbumin, which method comprises oligomerising α-lactalbumin in the molten globule-like state.

The expression "biologically active" as used herein means that the α-lactalbumin is able to induce apoptosis in tumour cells and/or has a bactericidal effect not seen with monomeric α-lactalbumin.

Methods for achieving the activation in accordance with the invention include those described below. For example, α-lactalbumin in the molten globule-like state is suitably contacted with the conversion reagent under conditions which allow ion exchange to take place. In particular therefore, α-lactalbumin in the molten globule-like state is applied to an ion exchange column, specifically an anion exchange column, which contains the conversion reagent. This may be achieved by eluting the column first with the conversion reagent. However, other reaction enviroments may produce similar effects and may be used.

A preparation of α-lactalbumin can contain material both the native and the molten globule-like state, the relative amounts of which will depend upon the method of purification used. It has been found that apoptosis inducing MAL will be produced when α-lactalbumin is applied to an ion exchange column in the presence of a conversion reagent.

However, it is preferable that a substantial portion, (i.e. greater than 50% w/w) of the α-lactalbumin applied to an ion exchange column is in the so-called molten globule-like state or that it is applied in conjunction with a reagent which will induce such a state.

The A-state or molten globule state of α-lactalbumin has native-like secondary structure but less well-defined tertiary structure (Kronman et al. 1965 Biochem, 4, 518–525; Dolgikh et al. Febs Lett, (1981) 136, 311–315 and FEBS Lett, (1984) 165:88–92, Ohgushi & Wada, 1983, A Febs Lett, 164:21–25). Molten globules are formed under acidic conditions and similar states are formed at neutral pH upon removal of the tightly bound $Ca^{2+}$-ion by ethylene diamine tetraacetic acid ("EDTA") by reduction of the disulfide bonds, or at elevated temperatures (Pfeil et al., 1987 Biochim Biophys Acta, 911:114–116; Kuwajima 1996 Faseb J. 1:102–109; Shulman et al., 1995 J. Mol. Bol. 253, 651–657).

Alteratively, α-lactalbumin can be produced recombinantly in a mutated form in which calcium binding domains are disrupted or destroyed. These recombinant proteins are more likely to form the molten globule-like state more readily. Furthermore, this method is advantageous since the purification of biologically active molecules from human milk is notoriously difficult, due to the abundance of highly bioactive molecules that contaminate the fractions. Recombinant production methods will avoid these difficulties.

Suitable targets for mutation so as to destroy calcium binding can be identified from the literature, but include mutation of the cysteine residues to other amino acids, such as alanine, which do not give rise to disulphide bridges. Examples of such mutations are described in Example 11 hereinafter.

DNA encoding the required recombinant α-lactalbumin can be inserted into suitable expression vectors which can then be employed to transform host cells, for example, prokaryotic cells such as E. coli or eukaryotic cells and in particular insect cells using conventional methods.

Depending upon the purification process or the source of the α-lactalbumin used in its production, it may be preferable to subject the α-lactalbumin to a pretreatment step which maximise amount of molten globule-like material. This may be effected by contacting the α-lactalbumin with a calcium chelating agent such as EDTA in order to remove excess calcium. This may be applied as a pre-treatment in which the α-lactalbumin is contacted with the chelating agent prior to elution down the ion exchange column, or alternatively, the EDTA may be added to the elution buffer.

Alternatively, the α-lactalbumin may be subjected to pre-treatment step involving exposure to a low pH, for example by addition of acidic material such as hydrochloric acid, so as to reduce the pH to the order of 2. In yet a further alternative, the α-lactalbumin is heated to an elevated temperature, for example a temperature from 25–120° C., suitably from 25 to 95° C., for example in excess of 70° C. Whether or not a pretreatment of this type is necessary in order to obtain optimum yields of active MAL can be determined by carrying out trial runs as illustrated hereinafter.

Suitable conversion reagents include one or more fatty acids or lipids, in particular those found in casein, and particularly the casein of human milk. A particularly suitable fatty acid has been found to be oleic acid, although others may be selected by routine testing methods. The fatty acid used as the conversion reagents may be used in pure form although a fraction of casein can provide a convenient source of this material.

Thus in a preferred embodiment, the invention provides a method for producing an oligomeric form of α-lactalbumin which comprises exposing a source of α-lactalbumin in a molten globule-like state to an ion exchange medium which has been pre-treated with casein or an active component thereof, and recovering oligomeric α-lactalbumin therefrom. The oligomeric α-lactalbumin derived therefrom is biologically active in that it can have activity in inducing apoptosis in tumour cells and/or have a bactericidal effect.

The casein or active component used in the pretreatment of the column may comprise casein or a fraction thereof which contains the fatty acids or a pure fatty acid.

Pre-treatment or "training" the ion exchange medium with oleic acid, for example as found in casein or active components thereof has been found to be particularly effective in increasing the yield of MAL, for example from various sources such as commercially available α-lactalbumin derived from both human and bovine milk.

The expression "active component" used herein refers to those one or more elements found in casein which produce the desired improvement in the process when used as a pre-treatment of the ion exchange column. It is known for instance, that casein contains a number of lipids and occasionally free fatty acids. The fatty acid content of casein is markedly increased if for example, the casein is frozen at 20° C. or subjected to hydrolysis reactions. It has been found that some of these elements are retained on a column which has been treated with casein. Such a column gives rise to an improved MAL production capability of the column.

As outlined above, a particularly preferred active component is oleic acid and this may be applied to the column in pure state in the pre-treatment step.

Casein from human milk contains long-chain polyunsaturated fatty acids in addition to oleic acid such as linoleic, γ-linoleic and arachidonic acid as well as triglycerides and lipids particularly phospholipids such as sphingomyelin. Any of these may be used in combination with the oleic acid, and may produce enhancement effects on the column. It would be a matter of routine to test which of these further elements or combination of elements produced enhanced effects and then the reagents could be used alone in place of the casein in order to pre-treat the ion exchange material.

Where casein or an active component used in the pre-treatment step, this may be isolated from milk derived from various mammals, such as humans, bovines, sheep or goats. Preferably however the casein or active component used in the pre-treatment are derived from human milk.

Isolation of casein fractions can be carried out using known methods, for example as described in WO 96/04929. The casein may be used directly or it may be frozen and later thawed prior to use. It has been found that casein which has been frozen or derived from frozen human milk is preferred in the pre-treatment step. Where the casein is used directly, it is preferable that it is first subjected to hydrolysis so as to hydrolyse some triglycerides present and so increase the amount of free fatty acid and in particular oleic acid, present before use in the pre-treatment step. This hydrolysis may be achieved for example by exposure of the casein to bile salts (J. Bitman et al., J. Ped. Gast. Nutr. 1983: 521–524).

Preferably the ion-exchange material used is arranged in a column as is conventional in the art. The various treatments can then be eluted through the column.

Suitably the oleic acid or casein or the active components thereof are eluted through a column containing new unused ion exchange material such as DEAE-TRIS-Acryl. Suitable elution buffers include tri-hydroxymethyl-aminomethane hydrochloride ("TRIS-HCl") with a pH of 8.5.

The amount of casein or the active components such as oleic acid or oleic acid composition applied to the column in this way may be small depending upon the volume of α-lactalbumin is required to be converted to MAL. For example, it has been found that only 30 mg of casein or casein equivalents per ml of column material can be used in the conversion of multiple 10 mg runs of bovine α-lactalbumin. After 6 runs (60 mg), the yield began to decrease, but some oligomeric α-lactalbumin was still obtained even after 10 runs.

In a preferred embodiment, the column is then washed with ion exchange buffer, such as the TRIS-HCl buffer mentioned above, without casein, and preferably also other buffers which are to be used in the process, such as a NaCl containing buffer to ensure that nothing unspecific will elute from the column when used in the process. Washing may be done several times.

The column may then be eluted with the source of α-lactalbumin as described above dissolved in the ion exchange buffer. The column comprises anion exchange material. Suitably a salt concentration gradient is induced in the column by elution with buffer containing suitable salts, for example those containing a suitable anion such as chloride. One such salt is sodium chloride. MAL containing fractions can then be isolated from the column. These fractions may be identified spectroscopically for example as illustrated hereinafter.

In the experiments illustrated hereinafter, it has been found that in general, the most active MAL fraction elutes first although some may be carried over into a second elution peak.

Using the process of the invention, MAL can be obtained from a wide variety of α-lactalbumin sources. For example it may be isolated from casein fractions or whey fractions of milk from any of the above-mentioned mammals or from commercially available monomeric α-lactalbumin which has been derived from any of these mammals. For example, monomeric bovine α-lactalbumin can be converted to therapeutic MAL in good yields, in some cases substantially completely, by treatment in accordance with the invention.

A pre-treated column can be used repeatedly to convert numerous fractions of α-lactalbumin to MAL. Once the column is exhausted or the conversion rate drops to unacceptable levels, the pre-treatment step can be repeated in order to restore the enhanced MAL production activity.

The reason why the "training" of the column in this way is so advantageous in MAL production is not entirely clear. It is possible that the components of the casein and in particular oleic acid retained on the column catalyses MAL production or stabilise α-lactalbumin in its oligomeric form.

Ion-exchange media and columns which have been trained or conditioned in this way form a further aspect of the invention, as does oligomeric α-lactalbumin obtainable using this method.

The invention will now be particularly described by way of example with reference to the accompanying diagrammatic drawings in which:

FIG. 3 shows an ion exchange chromatogram obtained by elution of a sample of human monomeric α-lactalbumin down a trained ion exchange column in accordance with the invention:

FIG. 4 shows an ion exchange chromatogram obtained by elution of a sample of bovine monomeric α-lactalbumin down a trained ion exchange column in accordance with the invention;

Figure 6A:
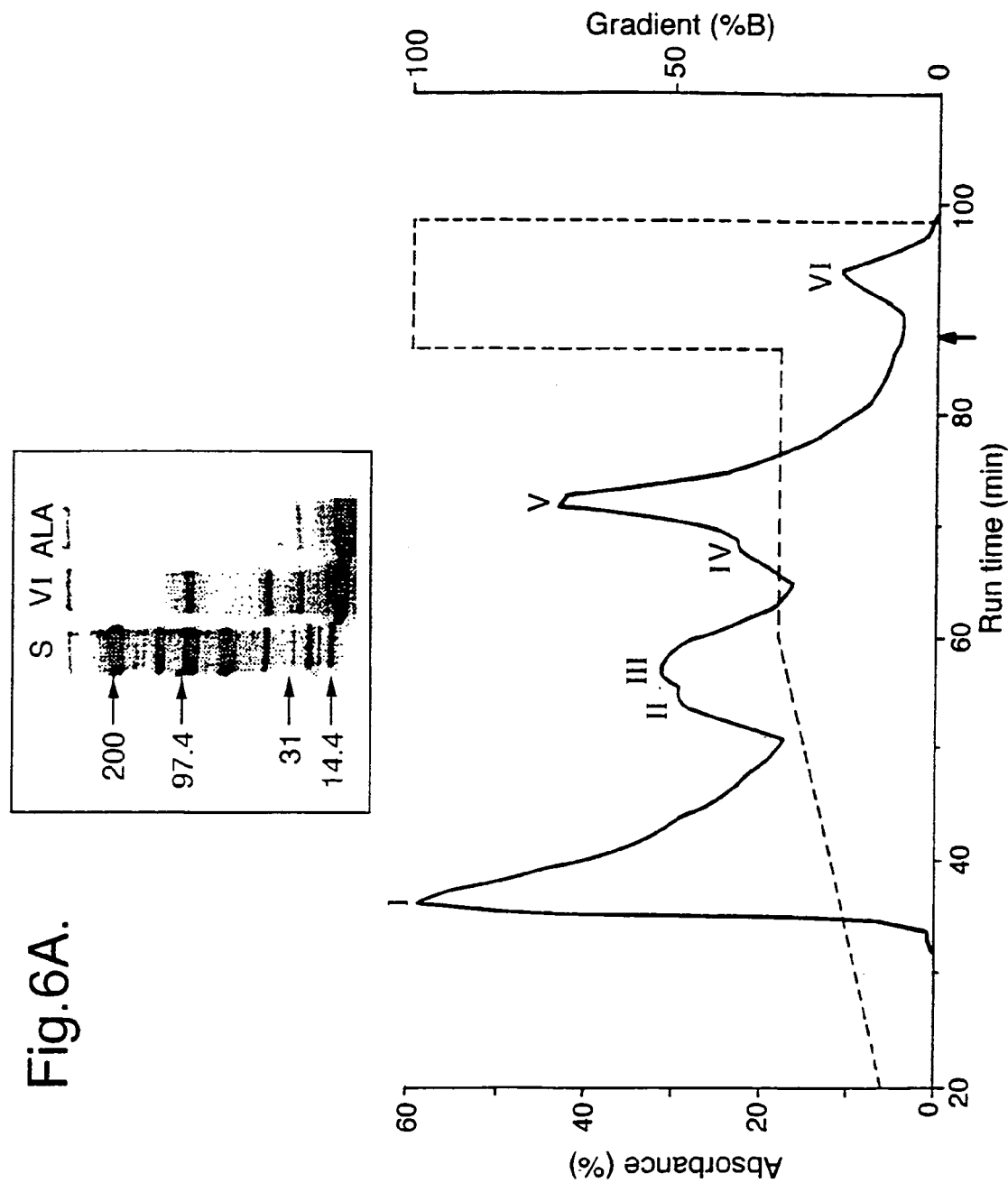
Figure 6B:
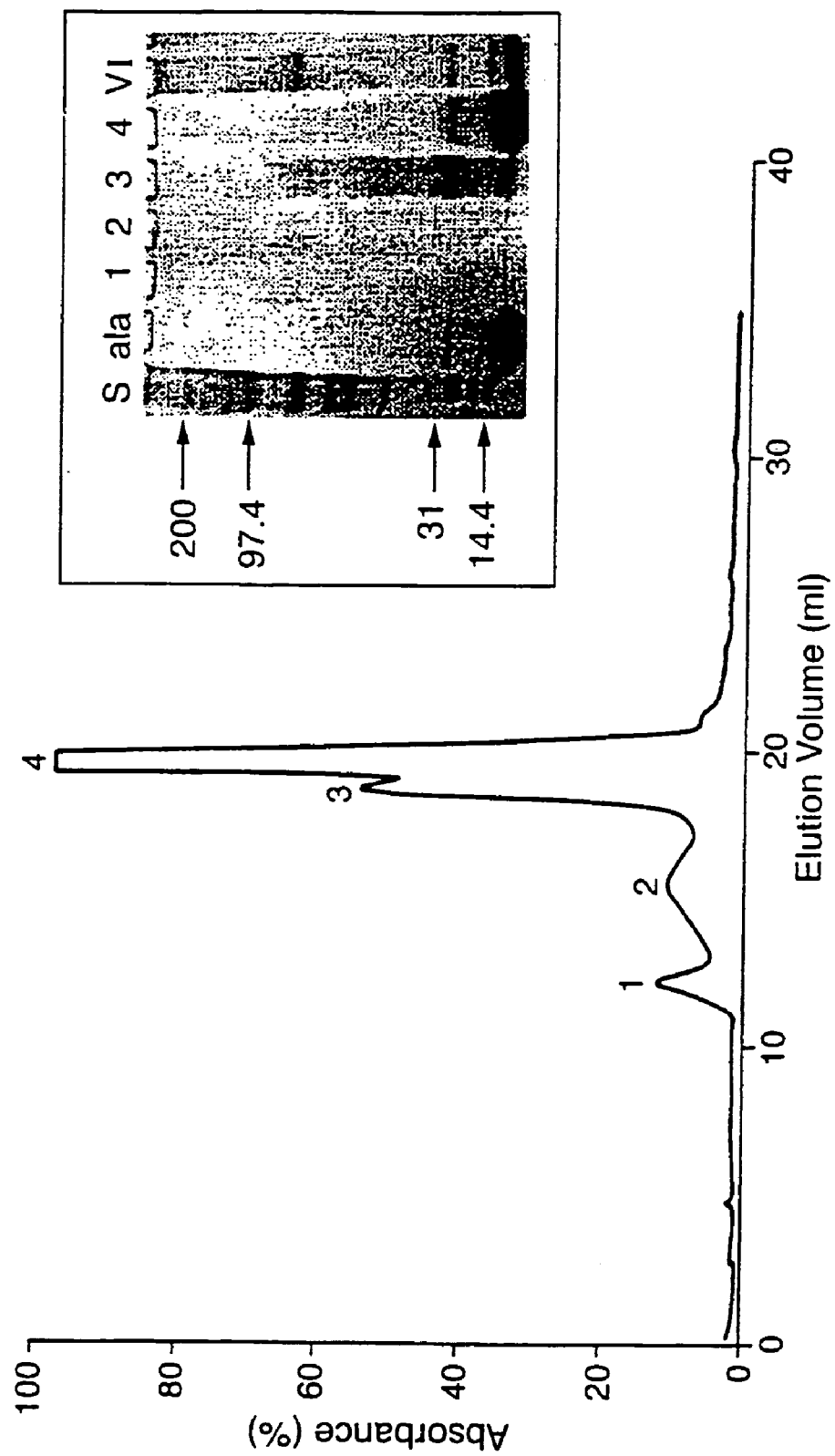
Figure 7:
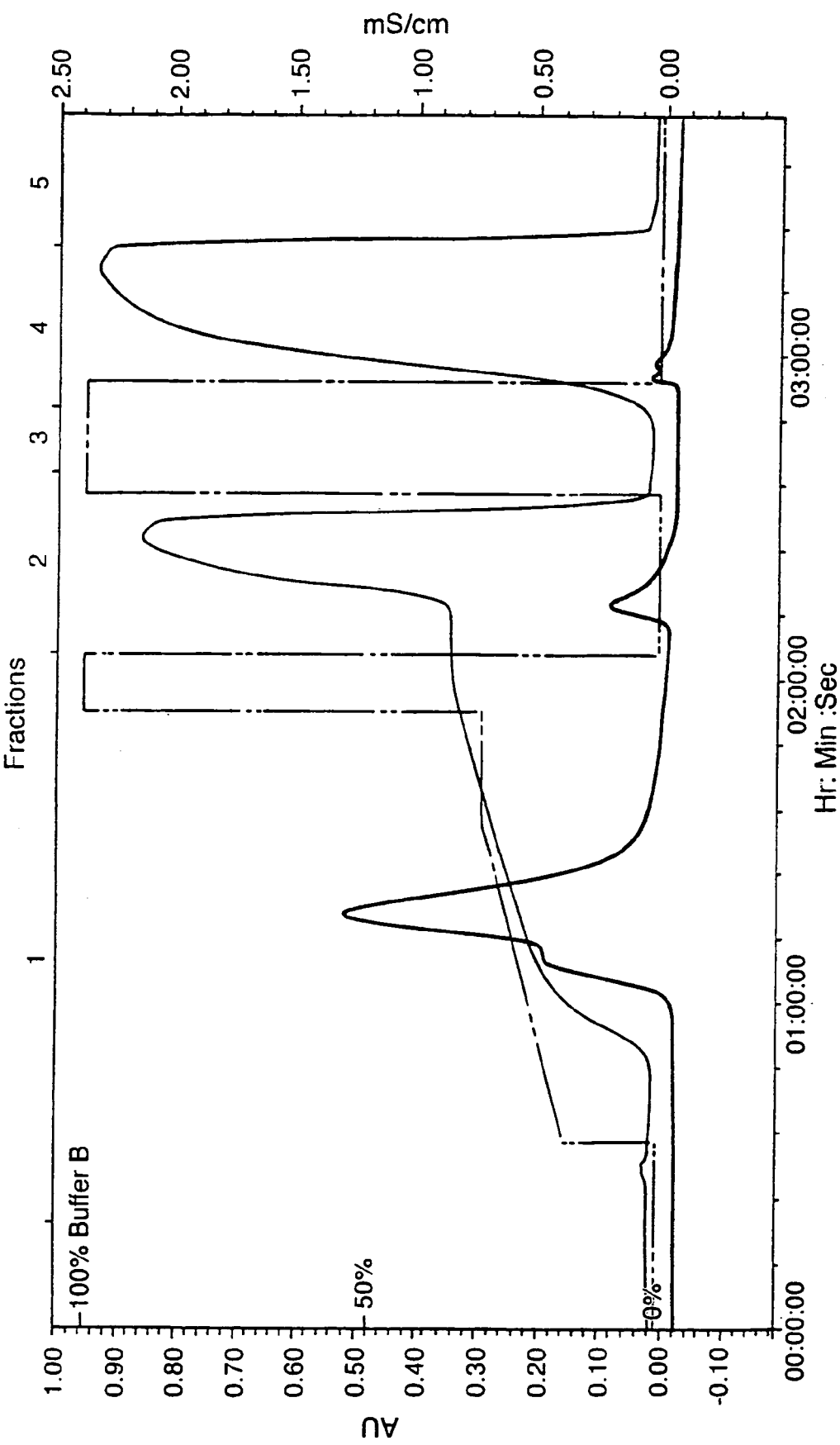
Figure 8:
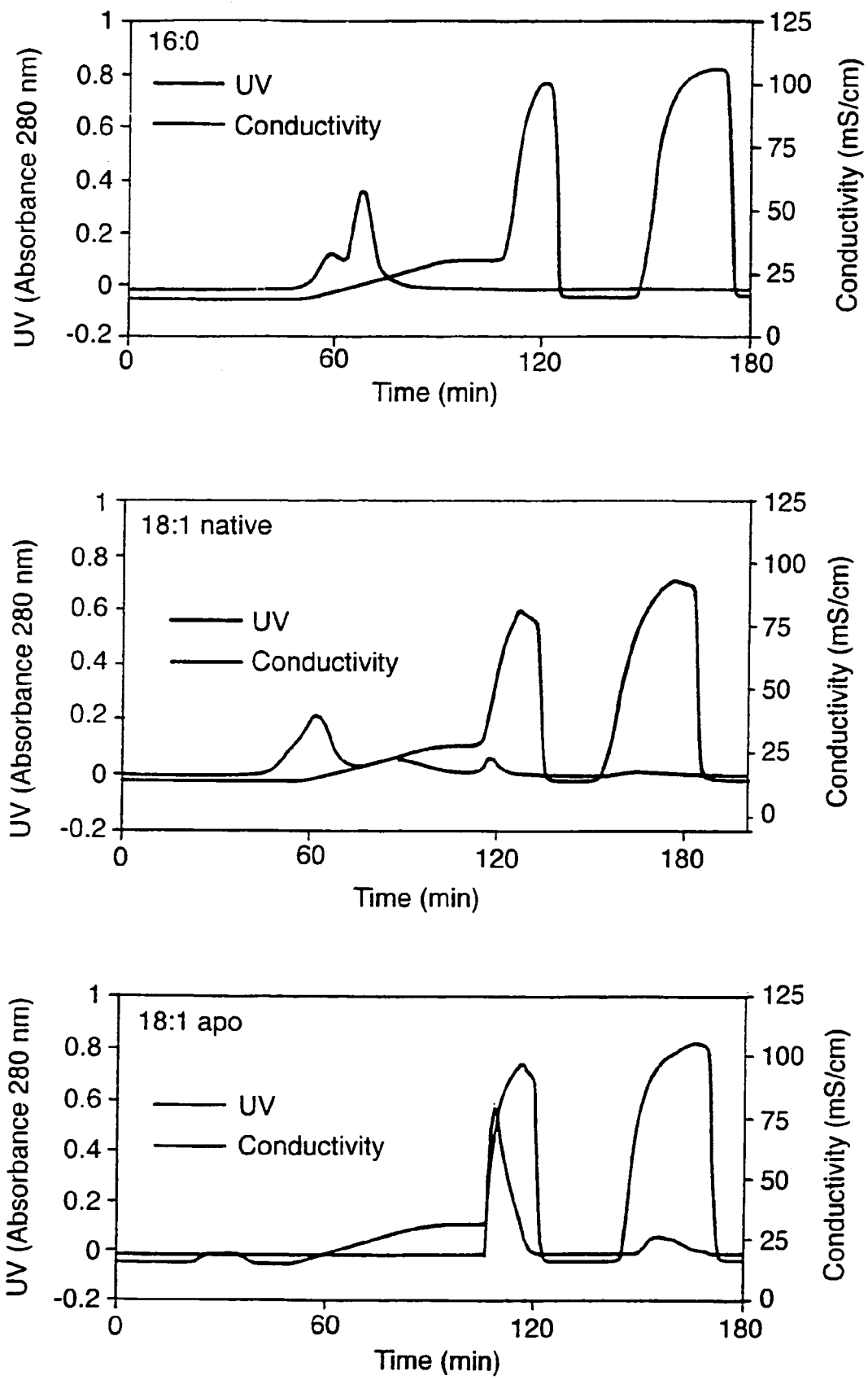

FIG. 5 A) is an ion-exhange chromatogram obtained by elution of a sample of human α-lactalbumin isolated from human milk by ammonium sulphate precipitation down a casein trained column: B) is an ion exchange chromatogram obtained by elution of a sample of EDTA treated human α-lactalbumin isolated from human milk by ammonium sulphate precipitation down a casein trained column C) is an ion exchange chromatogram obtained by elution of a sample of EDTA treated human α-lactalbumin isolated from human milk by ammonium sulphate precipitation down a casein trained column using buffers containing EDTA;

FIG. 6A) is an ion exchange chromatogram of human casein with the PAGE of the apoptosis inducing fraction (VI) inset; 6B is a size-exclusion chromatogram of the apoptosis inducing fraction (VI) with the corresponding PAGE of the different peaks inset; 6C is the 1.5 μM ANS fluorescence spectra of MAL and native α-lactalbumin; and 6D) shows the circular dichrosim spectra in the near UV region recorded at 25° C. for MAL and native α-lactalbumin;

FIG. 7 is an ion exchange chromatogram obtained by elution of a sample of EDTA treated human α-lactalbumin isolated from human milk by ammonium sulphate precipitation down a column trained with lipids extracted from a casein conditioned column; and FIG. 8 shows ion exchange chromatograms obtained by elution of a sample of EDTA treated human α-lactalbumin isolated from human milk by ammonium sulphate precipitation down columns trained with commercial free fatty acids where "Native" refers to untreated α-lactalbumin and "Apo" refers to EDTA treated α-lactalbumin.

In the ion exchange chromatograms shown in the Figures, the protein peak is indicated by a thick line.

Methodology

The ion exchange matrix used in the following examples was DEAE TRIS-Acryl M from BioSepra, France. The buffers comprised: Buffer A, 10 mM TRIS-HCl pH 8.5 and Buffer B, 10 mM TRIS-HCl with 1M NaCl pH 8.5.

The experiments were carried out at room temperature (22°). Sample was dissolved in 10 ml of buffer A.

Sample solution were injected onto the column at 1 ml/minute. The column was then eluted with buffer A for 10 minutes in order to get the sample on the column. Then a gradient of buffer B from 15–30% was induced. The gradient was held at 30% buffer B for 20 minutes during which time unwanted protein was eluted from the column. The concentration of buffer B was then increased to 100% which was held for 10 minutes. Where present, a MAL containing fraction eluted from the column during this period. The concentration of buffer B was reduced to 0% which was held for 20 minutes. Thereafter the concentration of buffer B was raised again to 100% and held for 20 minutes, during which a second MAL containing fraction was eluted. The concentration of buffer B was then reduced to 0% and the column eluted with buffer A only for a further 50 minutes.

Product was analysed using gel electrophoresis TRIS-Glycine PAGE gels 4–20%) as described previously in WO 96/04929, the content of which is hereby incorporated by reference.

COMPARATIVE EXAMPLE A

This example was carried out using a new and previously unused ion exchange matrix. Monomeric α-lactalbumin (ca. 25 mg) was added to the column in the manner outlined above. No detectable multimeric peaks were obtained on this occasion.

Figure 1:
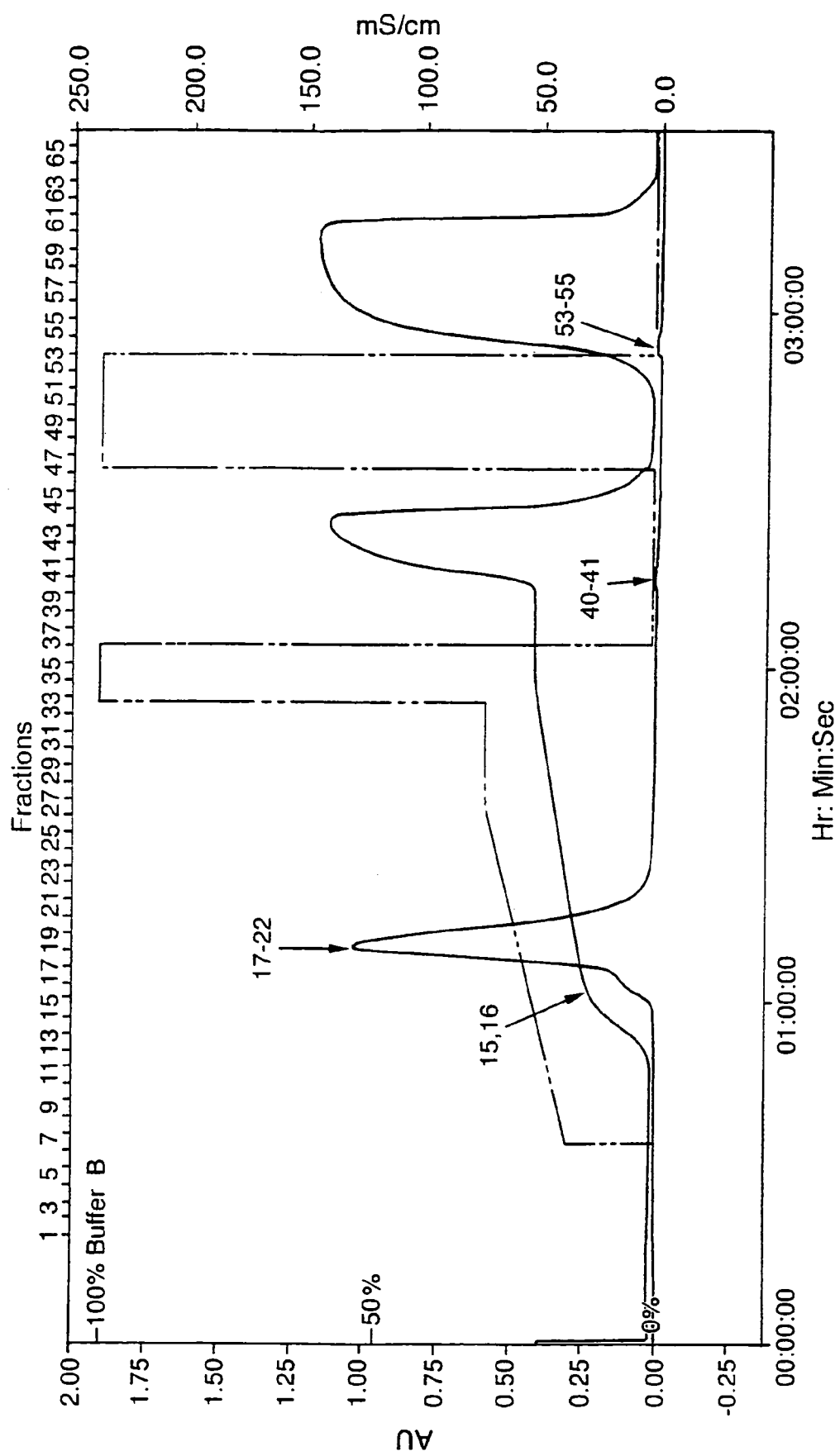
FIG. 1 shows an ion exchange chromatogram obtained by elution of a sample of pre-treated human monomeric α-lactalbumin down a clean ion exchange column.

Monomeric α-lactalbumin (20 mg) was subjected to a procedure used in the precipitation of casein. Specifically, the sample was mixed with 10% potassium oxalate and incubated overnight at 4° C. The pH was then lowered to 4.3 and the sample incubated at 32° C. for 2 hours. After overnight incubation at 4° C., the sample was added to the column. Although small multimeric peaks were detected (FIG. 1), no protein was found after dialysis and freeze drying of the product.

Figure 2:
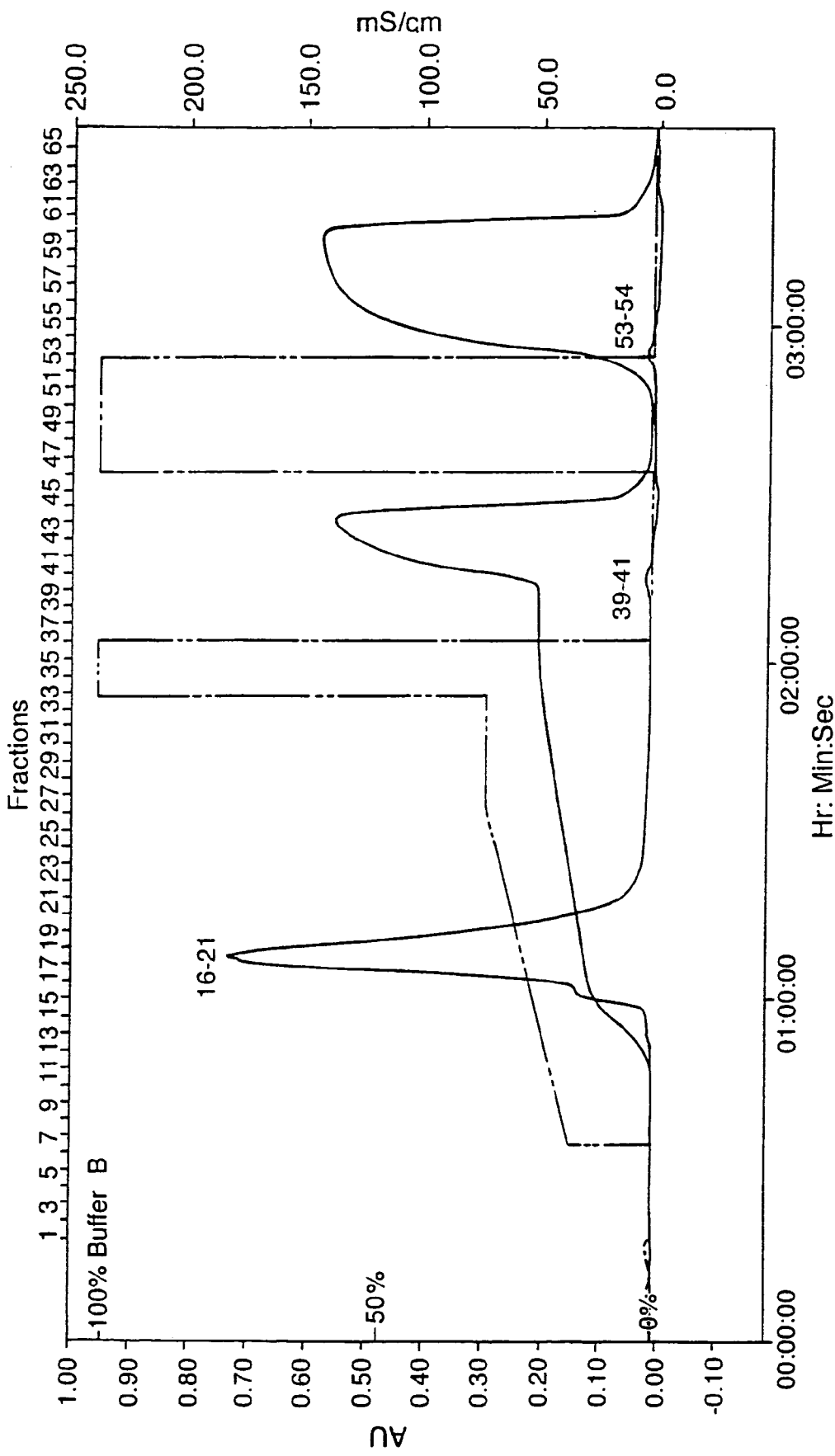
FIG. 2 shows an ion exchange chromatogram obtained by elution of a sample of pre-treated-human monomeric α-lactalbumin and lipids down a clean ion exchange column.

Monomeric α-lactalbumin (20 mg) was mixed with lipids extracted from whole human milk, subjected to the casein precipitation procedure outlined above, and added to the column. Again small multimeric peaks were detected but no protein was found after dialysis and freeze drying (FIG. 2).

EXAMPLE 1

In this example, 300 mg of casein derived from human milk was run on a fresh unused ion exchange matrix. The matrix was then washed with two runs of buffer A. Untreated commercially available (Sigma) monomeric human α-lactalbumin (8 mg) was added to the column. Two multimeric peaks were found (FIG. 3). Four further samples were run down this column and all gave two multimeric peaks.

COMPARATIVE EXAMPLE B

Example A above was repeated using a different sample of unused matrix and with monomeric commercially available (Sigma) bovine α-lactalbumin samples. None of the samples gave any multimeric peaks.

EXAMPLE 2

Example 1 above was repeated using monomeric bovine α-lactalbumin in place of human α-lactalbumin. Two clear multimeric peaks were obtained (FIG. 4).

EXAMPLE 3

Supplies of α-lactalbumin were obtained from various sources including commerically available human and bovine α-lactalbumin (Sigma) and α-lactalbumin isolated from human milk by ammonium sulphate precipitation of all proteins except α-lactalbumin, and then running the supernatant on a phenyl-sepharose column.

Figure 5A:
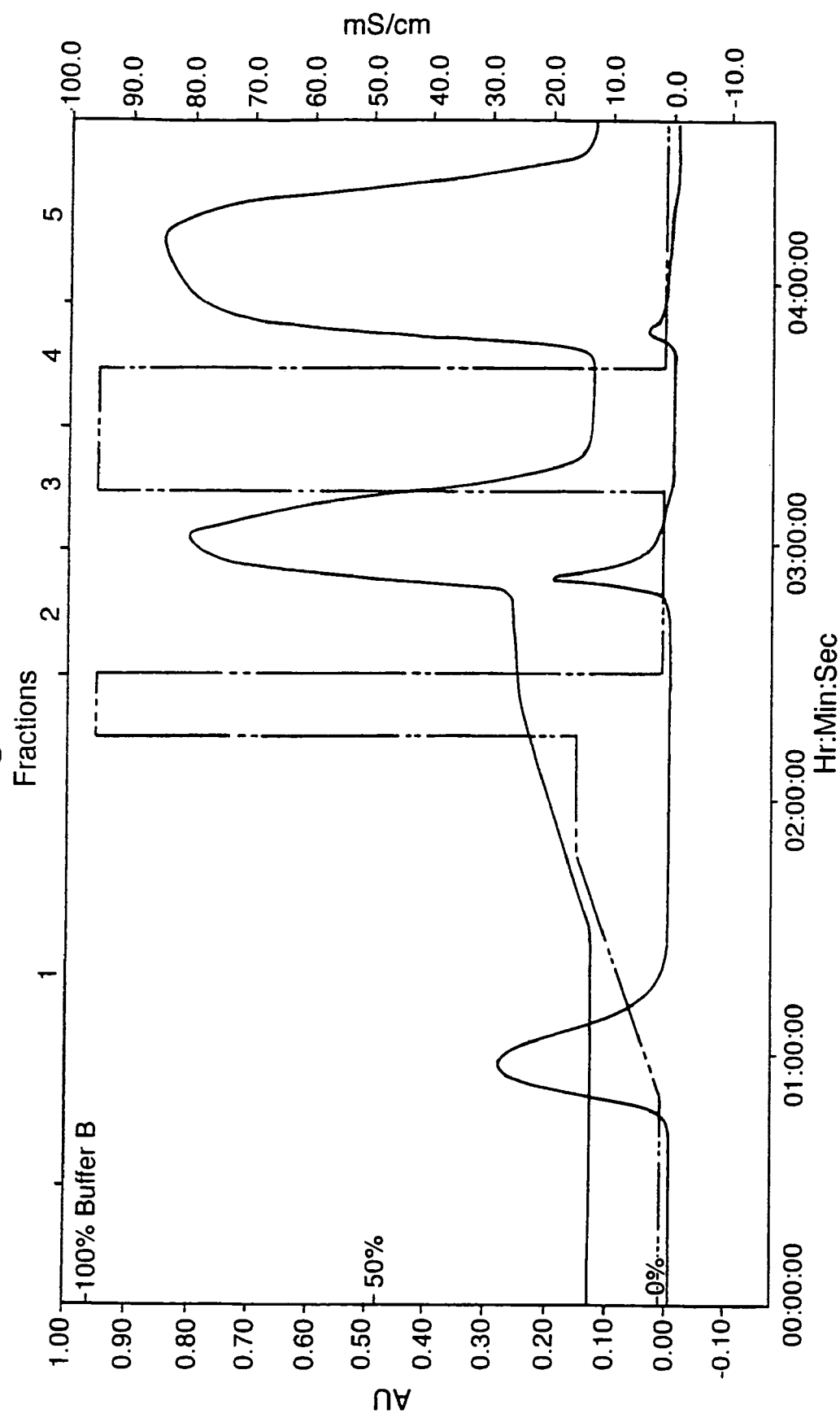
Figure 5B:
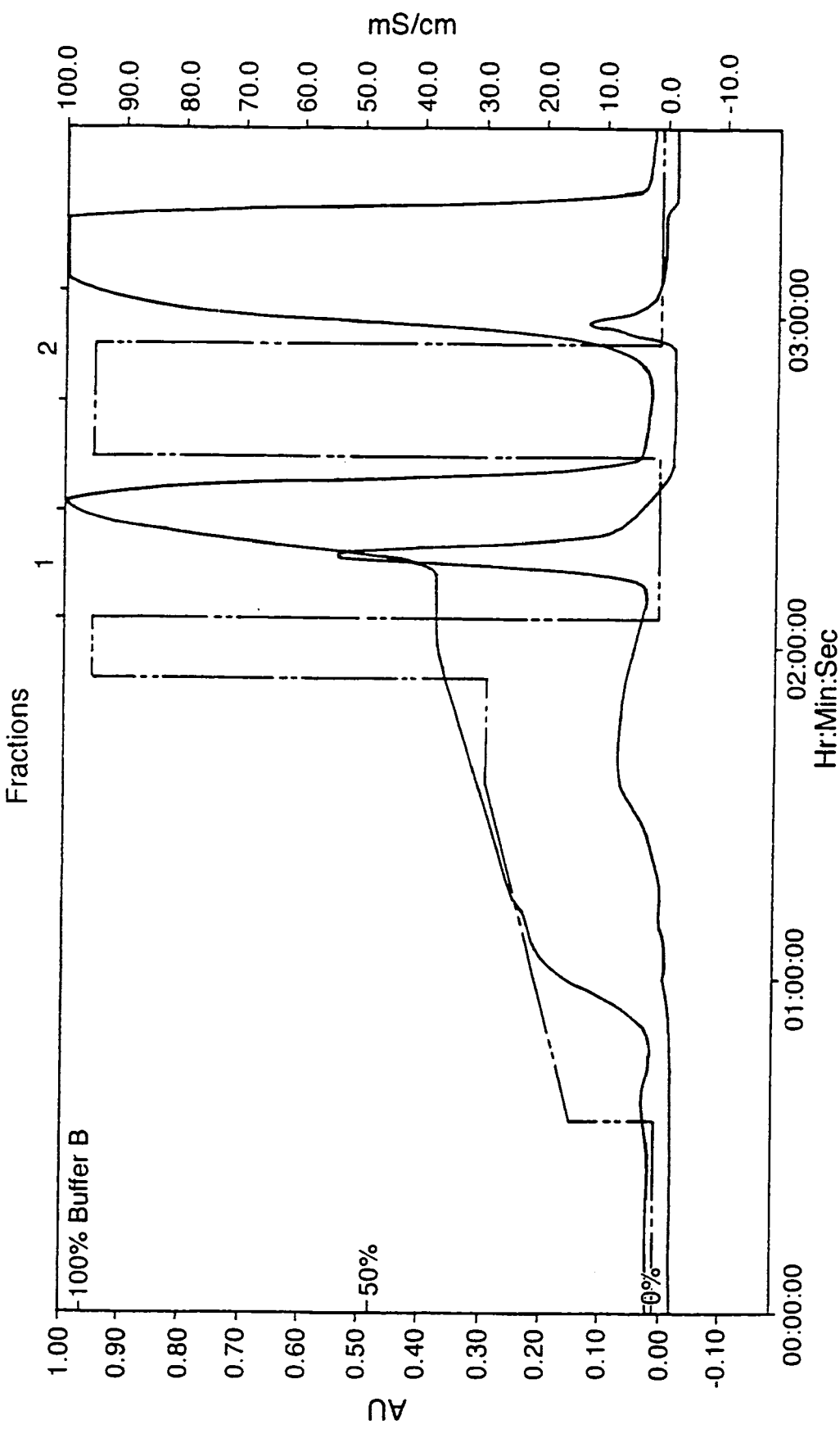
Figure 5C:
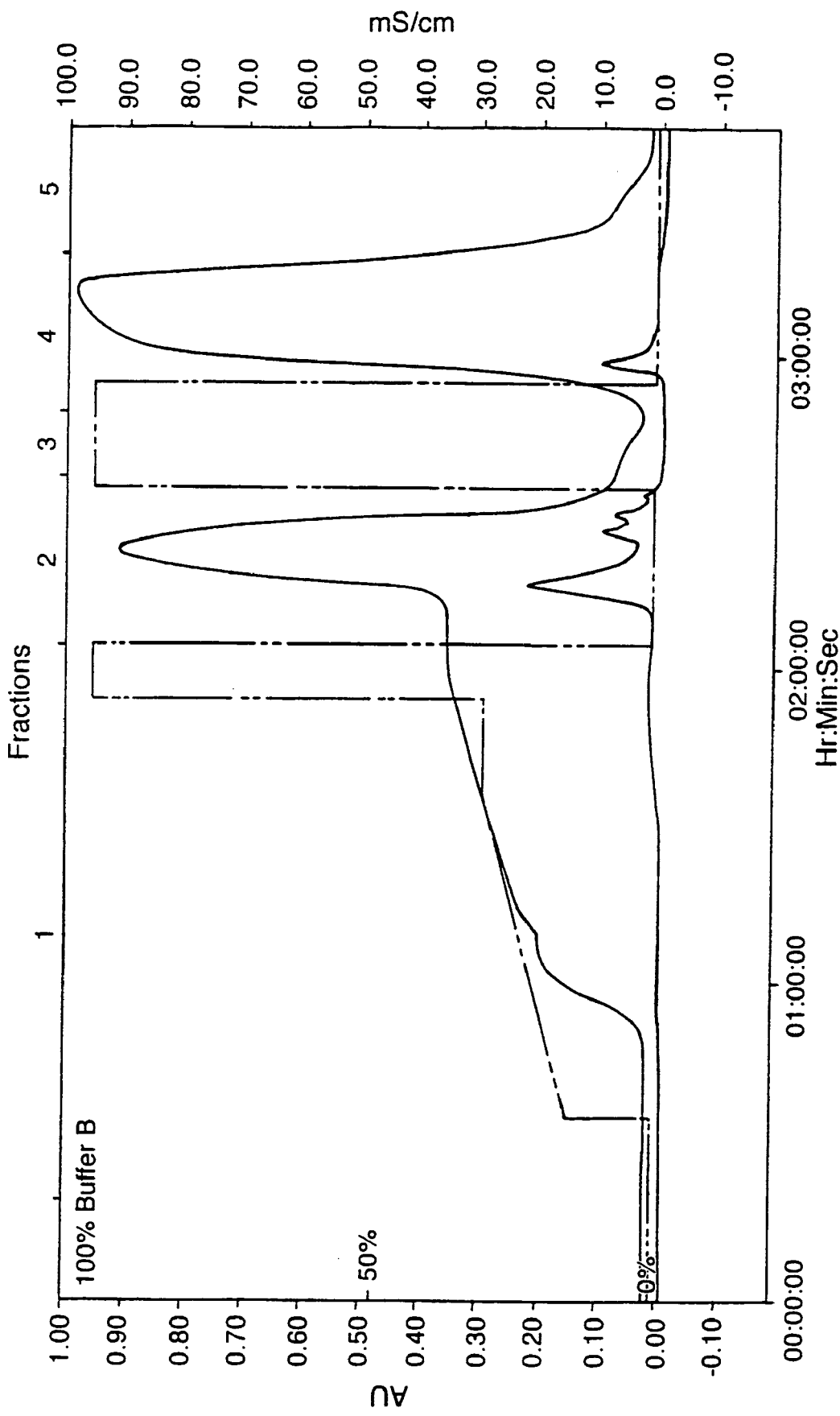

The samples were eluted down a column as described in Example 1 (FIGS. 3 and 5A). A second group of samples were pre-treated with EDTA by adding 7 mg of the α-lactalbumin to 10 ml of Buffer A containing 1 mM of EDTA. The mixture was left at room temperature for about 3 hours and was then added to the trained column and run using the buffers set out in Example 1 (FIG. 5B).

A third group of samples were treated with an EDTA containing buffer as described above and then run using EDTA buffers (FIG. 5C).

The two peaks which are believed to contain MAL were kept separately and tested individually. Testing was carried out as described hereinafter in Example 4. Representative results are set out in Table 1.

TABLE 1

| Source of α-lactalbumin | EDTA addition | MAL Peak tested | Dosage | Viability of tumour cells* |
|---|---|---|---|---|
| Commercial human α-lactalbumin | Untreated | 1 | 0.5 mg/ml | 0% |
|  |  |  | 1.0 mg/ml | 0% |
|  |  | 2 | 1.0 mg/ml | 0% |
| Human α-lactalbumin[+] | Untreated | 1 | 1.0 mg/ml | 79% |
|  |  | 2 | 1.0 mg/ml | 95% |
|  | EDTA pre-treated | 1 | 1.0 mg/ml | 0% |
|  |  | 2 | ca. 1.5 mg/ml | 98% |
|  | EDTA pre-treatment + EDTA buffer | 1 | 0.5 mg/ml | 0% |
|  |  |  | 1.0 mg/ml | 0% |
|  |  | 2 | 0.5 mg/ml | 89% |
|  |  |  | 1.0 mg/ml | 0% |

TABLE 1-continued

| Source of α-lactalbumin | EDTA addition | MAL Peak tested | Dosage | Viability of tumour cells* |
|---|---|---|---|---|
| Commercial bovine α-lactalbumin | untreated | 1 | 0.3 mg/ml | 50% |
|  |  |  | 0.5 mg/ml | 0% |
|  |  | 2 | 0.5 mg/ml | 98% |
|  |  |  | 1.0 mg/ml | 98% |

*Cell viability of tumour cells incubated with MAL as described below.
[+]Obtained using ammonium sulphate precipitation step as discussed above.

*Cell viability of tumour cells incubated with MAL as described below. [+]Obtained using ammonium sulphate precipitation step as discussed above.

These results indicate, that the first MAL containing fraction to elute is the most active. It is possible that the second peak contains only some residual MAL which 'leaked' from the first peak.

With certain samples, and in particular, those isolated from human milk using an ammonium sulphate precipitation step as outlined above, the removal of some calcium is necessary in order to ensure efficient conversion of monomeric α-lactalbumin to MAL.

EXAMPLE 4

Biological Data

The biological efficacy of the products obtained in the above Examples 1 and 2 above was tested using tumour cell lines as described in Håkansson et al (1995) supra. Cell lines were incubated with samples of the products at various concentrations in cell culture media at 37° C. for various time points. After incubation, the cells are harvested and the cell viability determined using a vital dye (trypan blue).

Oligonucleosome length DNA fragments were detected by agarose gel electrophoresis. Cells ($2 \times 10^6$) were lysed in 5 mM Tris, 20 mM EDTA, 0.5% Triton X-100 pH 8.0 at 4° C. for 1 hour and centrifuged at 13,000×g for 15 minutes. DNA was ethanol precipitated overnight in −20° C., treated with proteinase K and RNAse, loaded on 1.8% agarose gels and electrophoresed with constant voltage set at 50V overnight. DNA fragments were visualized with ethidium bromide using a 305 nm UV-light source and photographed using Polaroid type 55 positive-negative film.

Analysis of the results revealed the occurrence of DNA fragmentation in all cases, indicative of apoptosis.

The activity of the products of the above Examples 1 and 2 was similar to that obtained using protein isolated from human milk casein as described by Håkansson et al (1995) supra.

EXAMPLE 5

Further Analysis of MAL

A further set of experiments were undertaken in order to further characterise MAL.

Frozen human milk was thawed and centrifuged (Sorvall RC-5B refrigerated superspeed centrifuge, Du Pont Instruments, Wilmington Del., USA) at 2500×g for 15 minutes; the upper fat layer was removed. Casein was isolated by an overnight incubation at +4° C. with 10% potassium oxalate followed by a second overnight incubation at +4° C. after lowering the Ph to 4.3 using 1 M hydrochloric acid and heating the solution to 32° C. for 2 hours. The casein precipitate was harvested by centrifugation at 5000×g for 15 minutes, washed by 3–5 cycles of certrifugation and resuspension in distilled water and lyophilized. Casein was further fractionated on an ion-exchange column (14 cm×1.5 cm) packed with DEAE-TRIS-Acryl M (BioSepra, France) attached to a Biologic chromatography system (Biorad laboratories, Alfred Nobel Drive, Hercules, Calif., USA) using an increasing gradient of NaCl. The run was under the following conditions: buffer A: 10 mM TRIS-HCl pH 8.5; buffer B: buffer A containing 1 M NaCl/L. Gradient program: From start to 15 ml, 0% B; from 15 to 55 ml, 0–15% B; from 55 to 75 ml, 15% B; at 75 ml, 100% B for 10 min; from 85 to 115 ml, 0% B; at 115 ml, 100% B for 20 min; from 135 to end 0% B. The flow rate was 1 ml/min and the fraction size was 0.5 ml. The peaks was monitored by absorbance at 280 nm. The elute was desalted by dialysis (Spectra/Por, Spectrum Medical Industries, Laguna Hill Calif., USA, membrane cut off 3.5 kD) against distilled water for at least 48 h and lyophilized.

MAL eluted as a single peak after 1M NaCl.

Analytical PAGE was performed using 4–20% polyacrylamide precast gels on a Bio-Rad Mini Protean II. Each lyophilized fraction (5–10 mg/ml) was suspended in 10 μl of sample buffer 13.1% 0.5 M Tris/HCl, pH 6.8, 10.5% glycerol, 1.2% SDS and 0.05% Bromophenol Blue, and loaded on to the gel, which was run in Tris-glycine buffer (pH 8.3) with 0.1% SDS at 200 V constant voltage for about 40 min. Proteins were stained with 0.1% Coomassie Blue solution.

Size exclusion chromatography was effected by gel filtration, performed on a Pharmacia Sepharose 12 (S-12) gel filtration column in 10 mM TRIS-HCl 7.5 with 0.15M NaCl, and monitoried by UV absortion at 280 nm. The flow rate was 0.3 ml/min and the fraction size was 0.5 ml. Observed peaks were collected and desalted by dialysis against distilled water.

N-terminal amino acid analysis of MAL following the gel filtration described above using Edman degradation was performed in an automated pulse-liquid sequencer (Applied Biosystems model 477A). The results, shown in Table 2, confirm the identity of MAL to human α-lactalbumin.

TABLE 2

N-terminal amino acid sequence of the protein bands of MAL. The sequence of α- lactalbumin (HLA) is also shown.

HLA

14 Kda;  Lys-Gln-Phe-Thr-Lys-Cys-Glu-Leu-Ser-Gln-
-Leu-Leu-Lys-Asp-Ile-Asp-Gly-Tyr-Gly-Gly-
-Ile-Ala-Leu-Pro-Pro-Leu-Ile-Asp-Thr-Met

MAL 14 kDa;  Lys-Gln-Phe-Thr-Lys-Unk-Glu-Leu-Ser-Gln-
-Leu-Leu-Lys-Asp-Ile-Asp-Gly-Tyr-Gly-Gly-
-Ile-Ala-Leu-Pro-Pro-Leu-Ile-Asp-Thr-Met- 30 kDa;  Lys-Gln-Phe-Thr-Lys-Unk-Glu-Leu-Ser-Gln- 60 kDa;  Lys-Gln-Phe-Leu-Lys-
Arg Pro Lys Thr Pro 100 kDa;  Lys-Gln-Phe-Thr-Unk-Unk-Glu-Leu-Unk-Gln-
Asn Ile         Ser    Val
Tyr    Asn

Fractions of MAL:

Peak 1  Lys-Gln-Phe-Thr-Lys-Unk

Peak 2  Lys-Gln-Phe-Thr-Lys-Unk

Peak 3  Lys-Gln-Phe-Thr-Lys-Unk

Peak 4  Lys-Gln-Phe-Thr-Lys-Unk

Unk, indicates unknown; according to published results, residue 6 in α-lactalbumin is cysteine. Residues shown below the 60 and 100 kDa sequence of MAL are other possible candidates.

These techniques showed that the protein component of MAL consisted of α-lactalbumin monomers as well as oligomers of different molecular size (FIGS. 6A and B).

ANS fluorescence emission spectra were recorded between 400 and 700 nm (step 1 nm) with excitation at 385 nm. Both the excitation and emission bandpass was set to 5 nm. The concentration of the protein solutions was 1.0 mg/ml, corresponding to 70 μM monomer, in 10 mM potassium phosphate buffer at pH 7.5.

Figure 6C:
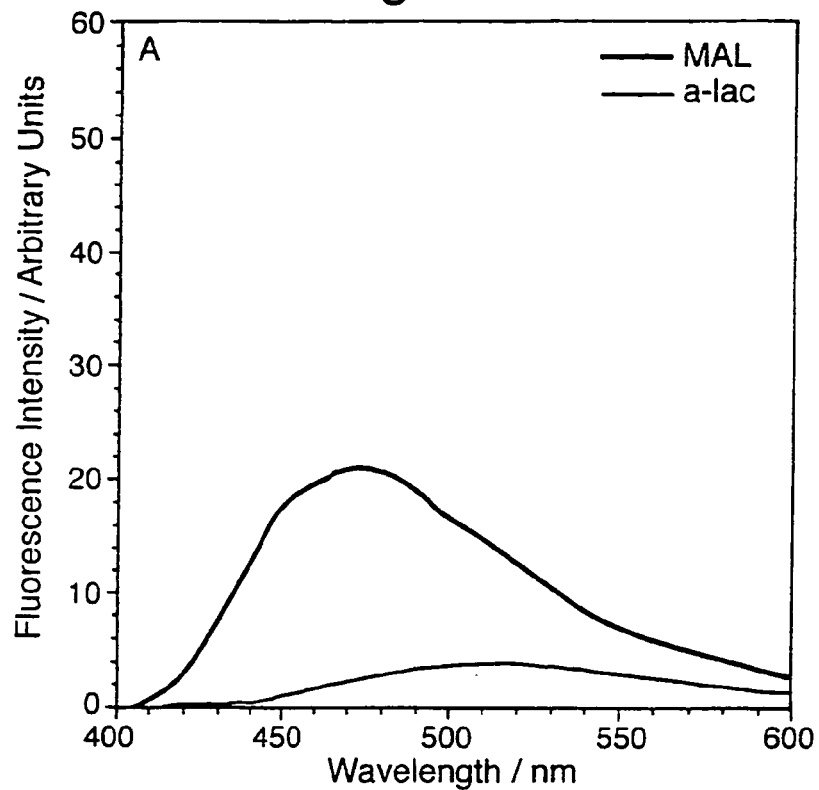

It was found that the ANS spectrum for MAL was blue shifted compared to the spectrum of native monomeric α-lactalbumin, with the intensity maximum at 475 nm and increased quantum yield indicating that ANS is bound by MAL (FIG. 6C). Further analysis was carried out using Circular Dichroism spectroscopy. Circular Dichroism (CD) spectra were obtained using a JASCO J-720 spectropolarimeter with a JASCO PTC-343 Peltier type thermostated cell holder. Quartz cuvettes were used with 1 cm path length. The proteins were dissolved in 10 mM potassium phophate buffer at pH 7.5 and the extract protein concentrations were determined using amnio acid analysis after acid hydrolysis.

Near UV spectra were recorded for between 300 and 240 nm. The wavelength step was 1 nm, the response time 4 s and the scan rate was 10 nm per minute. Six scans were recorded and averaged for each spectrum. Baseline spectra were recorded with pure buffer in each cuvette and subtracted from the protein spectra. The mean residue ellipticity $\theta_m$, was calculated from the recorded ellipticity, $\theta$, as $$\theta_m \theta/(c \cdot n \cdot l)$$

where c is the protein concentration in M, n the number of residues in the protein (123 in this case) and l the path length in m.

Figure 6D:
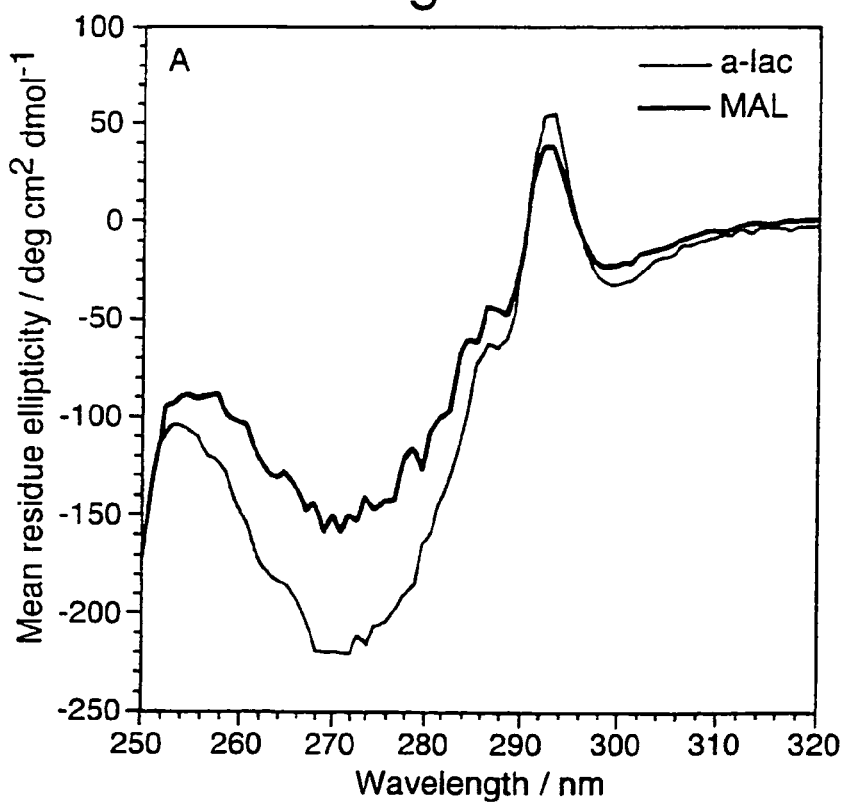

By near UV CD, MAL showed a minimum at 270 nm arising from tyrosine residues and a maximum at 294 nm arising from tryptophan residue, and was virtually identical to native α-lactalbumin, but with a lower signal. This indicates that the motion of tyrosines and tryptophanes is less restrained in MAL compared to native ∝-lactalbumin (FIG. 6D).

These spectroscopic analyses showed that MAL consisted of partially unfolded α-lactalbumin in the molten globule-like state.

This indicates that is should be possible to make MAL from monomeric α-lactalbumin under conditions that induce adequate folding changes.

EXAMPLE 6

Conversion of Monomeric α-Lactalbumin to MAL

Monomeric α-lactalbumin was purified from human milk by ammonium sulphate precipitation. The ammonium sulphate was added as a salt, 264 g/1 milk, and the mixture was incubated overnight at +4° C. The mixture was then centrifuged (Sorvall RC-5B refrigerated superspeed centrifuged, Du Pont Instruments, Wilmington Del., USA) at 5000×g for 15 minutes. The whey fraction was collected, lyophilized and dissolved in 50 mM TRIS-HCI with 35 mM EDTA, pH 7.5 A 400 ml phenyl-sepharose column (Pharmacia Biotech, Björkgatan, Uppsala, Sweden) was packed in 50 mM TRIS-HCI with 1 Mm EDTA, pH 7.5 and 500 ml sample was loaded onto the column. The column was first eluted with 50 mM Tris/HCl TRIS-HCI with 1 mM EDTA, pH 7.5 and α-lactalbumin was then eluted from the column with 50 mM TRIS/HCI with 1 mM $CaCl_2$, pH 7.5.

For conversion of monomeric α-lactalbumin, samples were dissolved in 10 mM TRIS-HCI pH 8.5 (A buffer) prior to loading onto the column. Material that eluted at 1 M NaCl was collected, desalted by dialysis and lyophilized.

Monomeric α-lactabumin was subjected to ion-exchange chromatography under conditions identical to those used in the purification of MAL. Ten milligrams of α-lactalbumin was loaded onto a new column matrix which was then eluted as described above. This gave no converted material. This confirms the results reported in Comparative Example A above.

Monomeric α-lactalbumin in the native state and α-lactalbumin treated with EDTA were subjected to ion-exhange chromatography over a casein conditioned column. Native, monomeric α-lactalbumin was converted to the multimeric form and eluted at the same position as MAL, but the peak had no apoptosis-inducing activity. α-lactalbumin treated with EDTA completely converted to the oligomeric form and eluted as a single peak after 1 m NaCl at the same position as MAL. The converted α-lactalbumin material had significant biological activity when tested as described in Example 1.

Results from the casein conditioned column suggested that an additional factor present in casein (factor X) was required for MAL formation and eluted with α-lactalbumin at 1 M NaCl. Factor X was consumed as shown a decrease in MAL yield which was noted after six runs.

EXAMPLE 7

Identification of Factor X.

Factor X was identified by eluting the column matrix under conditions suitable for proteins or lipids. Extraction of unused matrix was included as a control. Column matrix conditioned with casein was eluted with 1 M NaCl, 10 mM EDTA, 4 M urea and 20% ethanol. The column was attached to a Biologic chromatography system and the running conditions were the same as for the purification of casein (described above).

Elution with 10 mM EDTA did not release detectable protein other than monomeric α-lactalbumin. Urea 4 M, NaCl 1 M, or ethanol (20%) released only residual oligomerized α-lactalbumin as detected with PAGE.

The column matrix was extracted with organic solvents (chloroform/methanol) and extracted lipids were analysed by TLC. New matrix contained small amounts of phospholipids and free fatty acids. The casein conditioned matrix contained phospholipids, diglycerides, cholesterol, free fatty acids and triglycerides, i.e. the same lipid classes as in human milk. After elution of the casein conditioned matrix with monomeric α-lactalbumin as described in Example 6 above, the free fatty acid content decreased suggesting that this component was consumed.

Lipids were extracted according to Zeisel et. al J. Nutr. 1986, 116, 50–58. Briefly, 2 ml of matrix were dissolved in 25 ml of sterile water were mixed with 125 ml of chloroform/methanol (1:2 vol/vol), the solutions were mixed at room temperature for 15 min, incubated on ice for one hour and centrifuged at 11 600×g for 10 min (Sorvall RC-5B refrigerated superspeed centrifuge, Du Pont Instruments, Wilminton Del., USA). The supernatants were aspirated. The pellets were resuspended in 150 ml of chloroform/methanol/water (1:2:0.8 vol/vol/vol) mixed for 2 min and centrifuged at 11 600×g for 10 min. The supernatants were transferred to separation funnels and 175 ml of chloroform/water (1:1 vol/vol) was added. The phases were allowed to separate overnight at room temperature. The organic phases were collected and evaporated to dryness under nitrogen.

The free fatty acid content of the extracts was analysed using thin layer chromatography (TLC). Lipids extracted from 2 ml of matrix were dissolved in 10 μl of chloroform and applied on silica plates. Standards (monoglycerides, diglycerides, cholesterol, fatty acids, triglycerides and cholesterol ester) were similarly applied. Lipids were separated using petroleum ether/diethyl ether/acetic acid/methanol (80:20:1:2 vol/vol/vol/vol), and the lipids were visualized by spraying the plates with phosphomolybdic acid followed by heating at 120° C. for approximately 10 min and identified by comparison with the known standards.

The column extracts were analysed using gas chromatography (GC). New matrix contained low amounts of C 16:0, C 18:1, C12:0 and C 14:0. Casein conditioned matrix contained high amounts of C 16:0 and C 18.1, and also some C:14. After elution with α-lactalbumin the casein conditioned matrix contained the same free fatty acid classes but in much lower amounts.

EXAMPLE 8

Conditioning of Column Using Lipids

The lipids extracted from the casein conditioned column were used to condition a clean ion-exhange matrix. Lipids extracted from a casein conditioned column were dissolved in 500 µl 95% ethanol before A buffer was added. The lipid solution was added to the column and one run of the program was done in order to distribute the lipids through out the column. There after 10 mg of monomeric α-lactalbumin in the molten globule-like state was added and the program was run again. α-lactalbumin eluted as a single peak at the same position as MAL, and was found to have apoptosis-inducing activity (FIG. 7).

EXAMPLE 9

Identification of C18 Fatty Acid as Factor X.

The TLC analysis of the matrix lipids suggested that free fatty acids were involved in the production of MAL. GC analysis showed that palmitic acid C 16:0 and oleic acid C 18:1 were bound to the matrix after conditioning with casein.

Fatty acids were added to a column containing new matrix.

Two mg of palmitic acid (C 16:0), stearic acid (C 18:0), oleic acid (C 18:1), or linoleic acid (C 18:2) was dissolved in 500 µl 95% ethanol and then A buffer was added. Each lipid solution was added to the column and one run of the program was done in order to distribute the lipids through out the column. After each conditioning, 10 mg of monomeric α-lactalbumin in the molten globule-like state was added and the program was run again.

Oleic acid conditioned matrix efficiently converted α-lactalbumin which eluted as a single peak at the same position as MAL. Stearic acid C 18:0 and palmitic acid C 16:0 had no effect (FIG. 8).

This indicates that oleic acid is factor X.

EXAMPLE 10

Biological Effects of Lipids Isolated from MAL

In order to confirm that lipids themselves were not responsible for the biological activity seen, MAL was subjected to extraction with organic solvents. Lipids were analyzed by TLC. MAL was shown to contain 10–25% lipids by weight of the same major lipid classes as human milk and casein conditioned matrix; triglycerides predominated, followed by free fatty acids, mono- and di-glycerides, and phospholipids. CG analysis of the free fatty acids showed that C 18:1 predominated followed by C 16:0 and C 14:0. The L1210 (CCL 219) cell line was obtained from the American Type Culture Collection (ATCC), cultured in 25 cm$^2$ flasks (Falcon, Becton Dickinson, N.J., USA) at a density of $2\times10^6$/well in RPMI 1640 supplemented with 10% fetal calf-serum, 2 mM glutamine, non essential amino acids, sodium pyruvat, 50 µl gentamicin/ml and for L1210 cells µM 2-mercaptoethanol, kept at 37° C. in a humidified atmosphere containing 5% $CO_2$, with change of medium every three days. The cells were harvested by centrifugation (200 g for 10 min). The cell pellet was resuspended in RPMI and seeded into 24 well plates (Falcon, Becton Dickinson, N.J., USA).

Lipids extracted from MAL as described above and from column matrix were dissolved in culture medium, lacking fetal calf serum, by sonication for 3 minutes in a bath sonicator (Branson 2200, Branson, Danbury, USA) and added to the cells. The final volume was adjusted with medium to 1 ml per well. Plates were incubated at 37° C. in 5% $CO_2$ atmosphere for 6 hours with addition of 50 µl of fetal calf serum to each well after 30 minutes. Medium without lipid served as control.

The cell viability was determined by trypan blue exclusion. Cells ($2\times10^6$) were harvested by aspiration resuspended in PBS (5 ml) and washed by repeated cycles of centrifugation and resuspension in PBS. The washed cell pellet was resuspended in 1 ml of PBS, 30 µl were mixed with 30 µl of a 0.2% trypan blue solution and the number of stained cells (dead cells) per 100 cells was determined by interference contract microscopy (Ortolux II).

The MAL lipids were tested for apoptosis-inducing activity using L1210 cells. The lipid concentration was defined in "MAL equivalents" as the amount extracted from a defined mass of MAL. MAL at 0.7 mg/ml induced apoptosis in L1210 cells as seen by reduction of cell viability and formation of DNA fragments. However, lipids from 0.5 or 1 mg of MAL had no effect on cell viability or DNA fragmentation. At 2.5 mg MAL lipid equivalents cell viability was reduced to 45% and DNA fragmentation was observed, but at higher concentrations the cells were killed the cells by necrosis, no DNA fragmentation was observed. MAL lipids were not active at concentrations when intact MAL killed the cells. The results are shown in Table 3.

TABLE 3

Effects of MAL Lipids and column Lipids on the viability of L1210 cells

| | Viability % TBE |
|---|---|
| Medium control | 99 |
| Lipids extracted from MAL | |
| 0.05 mg/ml* | 97 |
| 0.08 mg/ml** | 98 |
| 0.15 mg/ml# | 97 |
| Lipids extracted from casein conditioned column | |
| 0.05 mg/ml* | 96 |
| 0.08 mg/ml** | 99 |
| 0.15 mg/ml# | 98 |
| Mixing human α-lactalbumin with column lipids | |

| α-lactalbumin | column lipids | |
|---|---|---|
| 0.3 mg | 0.05 mg | 95 |
| 0.5 mg | 0.08 mg | 98 |
| 1.0 mg | 0.15 mg | 98 |

*corresponding to 0.3 MAL equivalents
**corresponding to 0.5 MAL equivalents
corresponding to 1.0 MAL equivalents Lipids extracted from casein conditioned matrix, 0.7 mg/ml, killed the cells by necrosis. Lipids from new matrix or from casein conditioned matrix after elution with α-lactalbumin had no effect on the cells even at 1 mg/ml. The lipids extracted from the casein conditioned matrix (0.5 mg/ml) were mixed with α-lactalbumin (1 mg/ml). The cells still died by necrosis, indicating that mixing of α-lactalbumin with lipid did not result in the apoptosis inducing multimeric form.

EXAMPLE 11

Expression of Recombinant α-Lactalbumin in Insect Cells

The entire human ala gene and its flanking sequences were isolated from a genomic library of human placental tissue constructed in bacteriophage λ L47 (Hall, L., Emery, D. C., Davies, M. S., Parker, D., and Craig, R. K. Organization and sequence of the human alpha-lactalbumin gene., Biochem J. 242: 735–742, 1987). The gene is 2.3 kbp, contains four exons and three introns, and is flanked by about 5 kbp sequence on both sides. The gene was regionally assigned to 12q13 by in situ hybridisation (Hall, L., Emery, D. C., Davies, M. S., Parker, D., and Craig, R. K. Organization and sequence of the human alphα-lactalbumin gene., Biochem J. 242: 735–742, 1987 and Davies, M. S., West, L. F., Davis, M. B., Povey, S., and Craig, R. K. The gene for human alpha-lactalbumin is assigned to chromosome 12q13., Ann Hum Genet, 1987).

Expression of human α-lactalbumin in *E. coli* was achieved by Peng et al. (Peng, Z. Y. and Kim, P. S. A protein dissection study of a molten globule., Biochemistry. 33: 2136–41, 1994). DNA comprising the four ala exons was synthesized using oligonucleotides corresponding to codons characteristic for *E. coli*. Transformation of *E. coli* BL21 was with a T7-polymerase based vector, providing the promoter, translation initiation and transcription termination site from the T7 bacteriophage. Mutations in ala encoding regions involved in folding and $Ca^{2+}$ binding have been constructed. The plasmid pALA carries the entire human ala gene, pALD- the α-domain gene of ALA, pALA-ala with the cysteine residues changed to alanine. pALA-AZ carries the ala sequence mutated to replace cysteines 61, 73, 77 and 91 with alanines (Peng, Z. Y. and Kim, P. S. A protein dissection study of a molten globule., Biochemistry. 33: 2136–41, 1994). In PALA-BZ the cysteines 6, 28, 111 and 120 were changed to alanines, and in pALA (28–111) a single disulphide bond between cysteines 28–111 remained while all other cysteines were changed to alanines. Mutational inactivation of the disulphide bridges in the β sheet and between the domains of the molecule destroy the $Ca^{2+}$ binding site (pALA-BZ).

Insect cells secrete human proteins if cloned in-frame into a vector with the appropriate signal sequence. The pMelBac vectors are baculovirus transfer vectors designed to direct the expression of recombinant proteins through the secretory pathway to the extracellular medium.

The entire ala sequence was amplified by pcr from the vector pALA, encoding the complete gene for human ala, and was ligated into the Baculovirus vector pMelBacB behind the melatonin signal. The pMelBacB carrying the ala insert was co-transfected with linearised Bac-N-Blue DNA into insect cells to allow homologous recombination and to produce viable virus. Recombinant plaques were formed in High Five cells, and α-lactalbumin secretion was detected.

Recombinant material obtained in this way can be subjected to oligomerisation in the native state and in the molten globule-like state in order to produce biologically active MAL.

The invention claimed is:

1. A method of producing a biologically active oligomeric form of α-lactalbumin, which method comprises contacting α-lactalbumin, which is in the molten globule-like state, with a conversion reagent selected from the group consisting of fatty acids and lipids, wherein said fatty acids and lipids are found in a milk fraction containing casein obtained from human milk, wherein said method results in the production of said biologically active oligomeric form of α-lactalbumin.

2. A method according to claim 1 wherein α-lactalbumin in the molten globule-like state is contacted with the conversion reagent in the presence of an ion exchange medium.

3. A method according to claim 1 wherein α-lactalbumin in the molten globule-like state is applied to an ion exchange column, which contains the conversion reagent.

4. A method according to claim 2 wherein the ion exchange medium is an anion exchange medium.

5. A method according to claim 3 wherein the ion exchange column has been eluted with the conversion reagent.

6. A method according to claim 1 wherein at least 50% w/w of the α-lactalbumin is in the molten globule-like state.

7. A method according to claim 6 wherein the α-lactalbumin is subjected to a pretreatment step in which the amount of molten globule-like material present is maximized.

8. A method according to claim 7 wherein the pretreatment step comprises contacting the α-lactalbumin with a calcium chelating agent.

9. A method according to claim 8 wherein the calcium chelating agent is ethylene diamine tetraacetic acid.

10. A method according to claim 7 wherein the pretreatment step comprises exposing the α-lactalbumin to a pH of 2.

11. A method according to claim 10 wherein hydrochloric acid is added to a pH of 2.

12. A method according to claim 8 wherein the pretreatment step comprises heating the α-lactalbumin to a temperature in excess of 25° C. up to 120° C.

13. A method according to claim 12 wherein the temperature is from 70° C. to 120° C.

14. A method according to claim 1 wherein α-lactalbumin is contacted with the conversion agent on an ion exchange column, and wherein α-lactalbumin is applied to the column together with a molten globule inducing reagent, which will induce α-lactalbumin to form the molten globule-like state.

15. A method according to claim 14 wherein the molten globule inducing reagent is a calcium chelating agent present in the elution buffer.

16. A method according to claim 15 wherein the calcium chelating agent is ethylene diamine tetraacetic acid (EDTA).

17. A method according to claim 1 wherein the fatty acid is oleic acid.

18. A method according to claim 1 wherein calcium-binding sites in the α-lactalbumin have been inactivated.

19. A method according to claim 18 wherein a cysteine residue of the α-lactalbumin is mutated to another amino acid so as to inactivate a calcium-binding site.

20. A method for producing an oligomeric form of α-lactalbumin which comprises exposing a source of α-lactalbumin to an ion exchange medium which has been pretreated with a milk fraction containing casein obtained from human milk, or a member selected from the group consisting of fatty acids and lipids found in a casein containing fraction obtainable from human milk, and recovering α-lactalbumin in an oligomeric form therefrom.

21. A method according to claim 20 wherein the active component of casein is oleic acid.

22. A method according to claim 21 wherein the oleic acid is in a purified form.

23. A method according to claim 20 wherein the ion exchange medium has been treated with a milk fraction containing casein obtained from human milk.

24. A method according to claim 23 wherein the ion exchange medium has been treated with a milk fraction containing casein obtained from human milk which fraction has been previously frozen, or a milk fraction containing casein which fraction has been derived from frozen human milk.

25. A method according to claim 23 or claim 24 wherein the casein used in the pretreatment of the ion exchange medium has been subjected to hydrolysis.

26. A method according to claim 20 wherein the α-lactalbumin applied to the ion exchange medium is in the molten globule-like state.

27. A method according to claim 26 wherein the α-lactalbumin is formed into the molten globule-like state by contacting it with a calcium chelating agent.

28. A method according to claim 27 wherein the calcium chelating agent is ethylene diamine tetraacetic acid.

29. A method according to claim 27 or claim 28 wherein the calcium chelating agent contacts the α-lactalbumin prior to contact with the ion exchange medium.

30. A method according to claim 28 wherein an elution buffer containing the calcium chelating agent and α-lactalbumin is contacted with the ion exchange medium.

31. A method according to claim 24 wherein the α-lactalbumin is subjected to a pretreatment step involving exposure to a low pH of the order of 2.

32. A method according to claim 24 wherein the α-lactalbumin is subjected to a pretreatment in which it is heated to a temperature in excess of 25° C. up to 120° C.

33. A method according to any one of claims 26 to 28 and 30 to 32 wherein the ion exchange medium is arranged in a column.

34. A method according to claim 26 wherein the ion exchange medium comprises Diethylaminoethanol (DEAE) TRISacryl.

35. A method according to claim 26 which comprises passing a milk fraction containing casein obtained from human milk or one or more members selected from the group consisting of fatty acids or lipids found in a casein containing fraction obtainable from human milk, in an ion exchange buffer along an ion exchange column, washing the column with ion exchange buffer, and then passing a source of α-lactalbumin dissolved in the ion exchange buffer along the ion exchange column in the presence of a salt concentration gradient.

36. A method according to claim 35 wherein the ion exchange buffer is TRIS (hydroxmethyl) aminomethane hydrochloride.

37. A method according to claim 35 or claim 36 wherein said salt concentration gradient is produced using an ion exchange buffer in which sodium chloride is dissolved.

38. A method according to claim 37 wherein the column is washed by elution of ion exchange buffer twice.

39. A method according to claim 1 wherein the α-lactalbumin comprises monomeric bovine α-lactalbumin.

40. A method according to claim 1 wherein the α-lactalbumin comprises monomeric human α-lactalbumin.

41. An ion exchange medium for use in the method of claim 1 or claim 20 said medium having been treated with a milk fraction containing casein obtained from human milk or a member selected from the group consisting of fatty acids or lipids found in a casein containing fraction obtainable from human milk.

42. An ion exchange medium according to claim 41 wherein the medium has been treated with an active component of casein containing milk fraction comprising oleic acid.

43. An ion exchange column which comprises an ion exchange medium as defined in claim 41.

44. A biologically active oligomeric form of α-lactalbumin obtained by contacting α-lactalbumin in the molten globule-like state, with a conversion reagent selected from the group consisting of fatty acids or lipids, wherein said fatty acids and lipids are found in a milk fraction containing casein obtained from human milk.

45. A method according to claim 18 wherein the calcium binding site is destroyed.

46. A biologically active oligomeric form of non-human α-lactalbumin, obtainable by contacting α-lactalbumin in the molten globule-like state, with a conversion reagent selected from the group consisting of fatty acids or lipids, wherein said fatty acids and lipids are found in a milk fraction containing casein obtained from human milk.

47. A biologically active oligomeric form of α-lactalbumin according to claim 46, wherein the α-lactalbumin is bovine α-lactalbumin.

48. A biologically active complex comprising an α-lactalbumin in which calcium binding sites or domains are inactive, and a conversion agent selected from the group consisting of fatty acids or lipids, wherein said fatty acids and lipids are found in a milk fraction containing casein obtained from human milk.

49. A biologically active complex according to claim 48 wherein the conversion agent is oleic acid.

* * * * *